(12) United States Patent
Canada et al.

(10) Patent No.: US 6,436,963 B1
(45) Date of Patent: Aug. 20, 2002

(54) 2-METHOXYIMINO-2-(PYRIDINYLOXYMETHYL) PHENYL ACETAMIDES WITH (DERIVATISED) HYDROXYALKYL DERIVATIVES ON THE PYRIDINE RING

(75) Inventors: Emily J. Canada; Robert P. Gajewski, both of Indianapolis; Christopher S. Galka; Neil V. Kirby, both of Carmel; Irene M. Morrison, Indianapolis; Jeannie R. Phillips, Indianapolis; Mary E. Pieczko, Indianapolis; Brent J. Rieder, Greenfield; Chrislyn M. Carson, Carmel; Zhengyu Huang, Carmel, all of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/943,263

(22) Filed: Aug. 30, 2001

Related U.S. Application Data

(62) Division of application No. 09/397,566, filed on Sep. 16, 1999, now Pat. No. 6,306,839

(60) Provisional application No. 60/100,601, filed on Sep. 16, 1998.

(51) Int. Cl.[7] ..................... C07D 401/06; A61K 31/444
(52) U.S. Cl. ..................... 514/332; 514/335; 514/336; 546/261; 546/266; 546/267; 546/14; 546/280.4
(58) Field of Search .............................. 546/261, 267, 546/266, 280.4, 14; 514/335, 332, 336

(56) References Cited

U.S. PATENT DOCUMENTS

| | | | |
|---|---|---|---|
| 3,228,950 A | 1/1966 | Renk et al. ............... | 546/291 |
| 5,021,581 A | 6/1991 | Clough et al. ............. | 546/309 |
| 5,089,510 A | 2/1992 | Tapolczay .................. | 514/345 |
| 5,157,037 A | 10/1992 | Schuetz et al. ............ | 514/269 |
| 5,185,342 A | 2/1993 | Hayase et al. ............. | 514/274 |
| 5,334,577 A | 8/1994 | Wenderoth et al. ......... | 504/130 |
| 5,442,063 A | 8/1995 | Takase et al. ............. | 544/333 |
| 5,466,693 A | 11/1995 | Warrington et al. ........ | 514/269 |
| 5,585,513 A | 12/1996 | Matthews et al. .......... | 560/60 |
| 5,770,614 A | 6/1998 | Murabayashi et al. ...... | 514/348 |
| 5,856,573 A | 1/1999 | Takase et al. ............. | 564/169 |
| 6,133,294 A | * 10/2000 | Kirby et al. .............. | 514/340 |

FOREIGN PATENT DOCUMENTS

| | | |
|---|---|---|
| CS | 415 630 | 9/1962 |
| DE | 1 373 314 | 10/1972 |
| DE | WO 00/76979 | 12/2000 |
| EP | 0 198 382 | 4/1986 |
| EP | 0 235 470 | 6/1986 |
| EP | 0 544 151 | 11/1992 |
| EP | 0 596 254 A1 | 5/1994 |
| EP | 0 661 269 | 12/1994 |
| EP | 0 693 477 | 7/1995 |
| EP | WO 96/37472 | 11/1996 |
| EP | WO 97/01538 | 1/1997 |
| EP | 0 781 764 A1 | 7/1997 |
| EP | WO 97/29088 | 8/1997 |
| EP | 0 816 331 | 1/1998 |
| EP | 0 848 685 | 6/1998 |
| EP | WO 98/23350 | 6/1998 |
| EP | WO 98/33772 | 8/1998 |
| EP | 0 891 975 | 1/1999 |
| EP | WO 99/25713 | 5/1999 |
| JP | 06026884 | 9/1995 |

OTHER PUBLICATIONS

Kelichl Imamura, et al; Preparation of Picolinamlde Derivatives and Pest Controllers Containing the Same as the Active Ingredient.

Makoto Tanlguchi, et al; Preparation of 3–Hydroxypicolinic Acid Amides and 2–Hydroxynlcotnic Acide Amides as Funglcides.

"The Strobllurin Fungicldes", Fungicidal Activity, 1998.

"Structure and Fungicidal Activities of 2–Methoxyimino–N–methyl–2–[2–(substituted pryidyloxymethyl)phenyl]acetamide Derivaties", J. Pesticide Sci. 23, 379–385 (1998).

Extended Summaries: IUPAC Congress, Pestic Sci 55: 343–389 (1999).

"Strobilurins: Evoluation of a New Class of Active Substantces", Angew Chem, Int. Ed. 1999, 38, 1328–1349.

* cited by examiner

*Primary Examiner*—Jane Fan
(74) *Attorney, Agent, or Firm*—Carl D. Corvin; Dugal S. Sickert

(57) ABSTRACT

The present invention provides novel 2-methoxyimino-2-(pyridinyloxymethyl)phenyl acetamide compounds with (derivatised) hydroxyalkyl substituents on the pyridine ring, their use as fungicidal compounds, and their use in fungicidal compositions comprising at least one of the 2-methoxyimino-2-(pyridinyloxymethyl)phenyl acetamide compounds as the active ingredient.

4 Claims, No Drawings

2-METHOXYIMINO-2-(PYRIDINYLOXYMETHYL) PHENYL ACETAMIDES WITH (DERIVATISED) HYDROXYALKYL DERIVATIVES ON THE PYRIDINE RING

PRIORITY CLAIM

This application is a divisional of and is based on non-provisional application Ser. No. 09/397,566 which was filed in the U.S. Patent and Trademark Office Sep. 16, 1999 now U.S. Pat. No. 6,306,839 and provisional application No. 60/100,601 which was filed in the U.S. Patent and Trademark Office on Sep. 16, 1998.

BACKGROUND OF THE INVENTION

The present invention provides novel 2-methoxyimino-2-(pyridinyloxymethyl)phenyl acetamide compounds with (derivatised) hydroxyalkyl substituents on the pyridine ring, their use as fungicidal compounds, and their use in fungicidal compositions comprising at least one of the 2-methoxyimino-2-(pyridinyloxymethyl)phenyl acetamide compounds as the active ingredient.

SUMMARY OF THE INVENTION

This invention provides novel 2-methoxyimino-2-(pyridinyloxymethyl)phenyl acetamide compounds of Formula (1), below Formula (1)

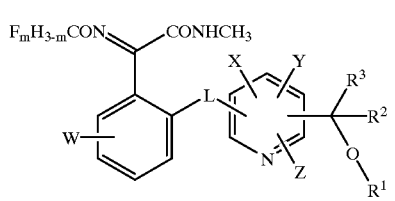

wherein m is an integer 0–3;

L is —O—, —CH$_2$—, —SO$_n$—, —CH$_2$O—, —OCH$_2$—, —CH$_2$S—, —SCH$_2$—, —CH=CH—, —C≡C—, or

wherein n is an integer 0–2;

X, Y, and Z are each independently H, C$_{1-6}$ alkyl, C$_{1-6}$ alkoxy, halo-C$_{1-6}$ alkyl, halo-C$_{1-6}$ alkoxy, halo, nitro, carbo-C$_{1-6}$ alkoxy, cyano, C$_{1-6}$ alkylthio, or halo-C$_{1-6}$ alkylthio;

W is H, halogen, C$_{1-4}$ alkyl, C$_{1-4}$ alkoxy, halo-C$_{1-4}$ alkyl, or C$_{1-4}$ alkylthio;

R$^1$ is H, C$_{1-6}$ alkyl, cycloalkyl, haloalkyl, alkoxyalkyl, alkenyl, alkynyl, haloalkenyl, haloalkynyl, trialkylsilyl, phenyl (optionally substituted by C$_{1-4}$ alkyl, halo, alkoxy, haloalkyl, or haloalkoxy), benzyl (optionally substituted by C$_{1-4}$ alkyl, halo, methoxy, haloalkyl, or haloalkoxy), alkylsulphonyl, optionally substituted benzenesulphonyl, trialkylphosphonyl, optionally substituted saturated or unsaturated 5 or 6 membered heterocycle, or —CO—R$^4$;

R$^2$ is H, alkyl (optionally, a C$_{1-6}$ alkyl), cycloalkyl, phenyl (optionally substituted by C$_{1-4}$ alkyl, halo, alkoxy, haloalkyl, haloalkoxy, alkoxycarbonyl, alkylcarbonyl, arylcarbonyl, or aryloxy), hydroxyalkyl, optionally substituted heterocycle, haloalkyl, optionally substituted naphthyl, or —CH$_2$OR$^5$;

R$^3$ is H, alkyl (optionally, a C$_{1-6}$ alkyl), cycloalkyl, phenyl (optionally substituted by C$_{1-4}$ alkyl, halo, alkoxy, haloalkyl, haloalkoxy, alkoxycarbonyl, alkylcarbonyl, arylcarbonyl, or aryloxy), hydroxyalkyl, optionally substituted heterocycle, haloalkyl, optionally substituted naphthyl or —CH$_2$OR$^5$;

or R$^1$ and R$^2$ together form a link of 1–3 atoms which form an optionally substituted heterocyclic ring containing one or more oxygen atoms;

or R$^2$ and R$^3$ together form an optionally substituted carbocyclic or heterocyclic ring;

R$^4$ is H, C$_{1-6}$ alkyl, cycloalkyl, haloalkyl, alkoxyalkyl, alkenyl, alkynyl, haloalkenyl, haloalkynyl, phenyl (optionally substituted by C$_{1-4}$ alkyl, halo, methoxy, haloalkyl, haloalkoxy), benzyl (optionally substituted by C$_{1-4}$ alkyl, halo, methoxy, haloalkyl, or haloalkoxy), alkoxy, or dialkylamino; and R$^5$ is alkyl (optionally, a C$_1$–C$_6$ alkyl), alkanoyl, optionally substituted benzoyl, alkylsulphonyl, or optionally substituted benzenesulphonyl.

The present invention also provides compositions comprising one or more compounds of Formula (1) in combination with phytologically-acceptable carriers and/or diluents. Methods for the use of compounds of Formula (1) and compositions comprising one or more compounds of Formula (1) are also provided.

DETAILED DESCRIPTION OF THE INVENTION

Throughout this document, all temperatures are given in degrees Celsius and all percentages are weight percentages, unless otherwise stated.

The term "halogen" or "halo" refers to F, Cl, I, or Br.

The term "alkyl", "alkenyl", or "alkynyl" refers to a straight chain or branched chain carbon radical containing the designated number of carbon atoms.

The term "alkoxy" refers to a straight or branched, chain alkoxy group.

The term "halo alkyl" refers to a straight or branched alkyl group substituted with one or more halo atoms. The term "halo alkoxy" refers to an alkoxy group substituted with one or more halo atoms.

The term "aryl" or "Ph" refers to a phenyl group. The term "substituted aryl" refers to a phenyl group substituted with C$_1$–C$_6$ alkyl, C$_1$–C$_6$ alkoxy, halo-C$_1$–C$_6$ alkyl, halo-C$_1$–C$_6$ alkoxy, halo, nitro, carbo-C$_1$–C$_6$ alkoxy, or cyano. The term "heteroaryl" refers to pyridyl, pyridinyl, pyrazinyl or pyridazinyl.

The term "Me" refers to a methyl group. The term "Et" refers to an ethyl group. The term "Pr" refers to a propyl group. The term "Bu" refers to a butyl group.

The term "EtOAc" refers to ethyl acetate.

The term "ppm" refers to parts per million. The term, "psi" refers to pounds per square inch.

The term "M.P." refers to melting point. The term "bp" refers to boiling point.

While all the compounds of this invention have fungicidal activity, certain classes of compounds may be preferred for reasons such as, for example, greater efficacy or ease of synthesis.

A preferred class includes those compounds of Formula (2), below

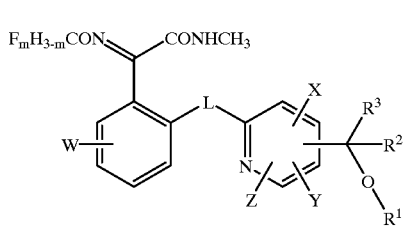

Formula (2)

wherein the substituents are as defined in Formula (1), above.

A more preferred class includes those compounds of Formula (3), below

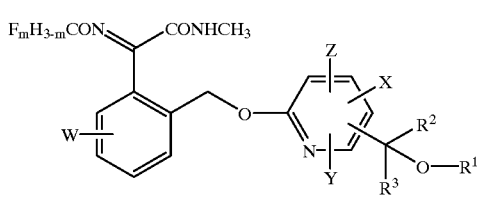

Formula (3)

wherein the substituents are as defined in Formula (1), above.

A next more preferred class includes those compounds of Formula (4), below

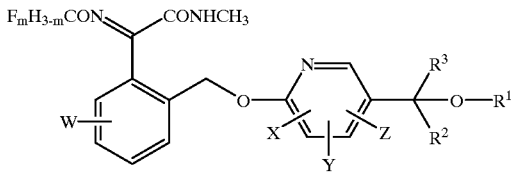

Formula (4)

wherein the substituents are as defined in Formula (1), above.

A next more preferred class includes those compounds of Formula (5), below

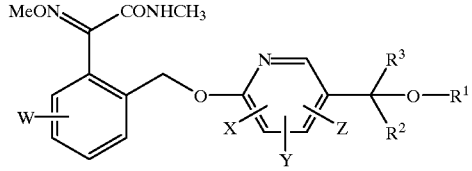

Formula (5)

wherein the substituents are as defined in Formula (1), above.

A next more preferred class includes those compounds of Formula (6), below

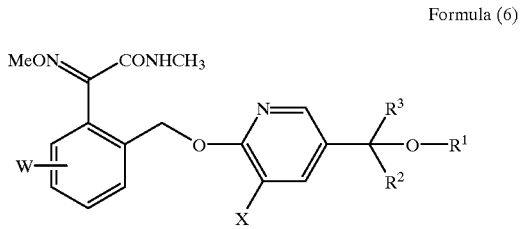

Formula (6)

wherein X is methyl, halo, or haloalkyl and the additional substituents are as defined in Formula (1), above.

Currently, it is sometimes preferred when $R^1$ is hydrogen, $C_{1-4}$ alkyl, formyl, alkanoyl, alkoxycarbonyl, dialkylaminocarbonyl, or dialkylphosphonyl and $R^5$ is H, $C_{1-4}$ alkyl.

Compounds of the present invention may be prepared by routes commonly known in the art using commercially available or readily synthesized starting materials. Such general procedures are described in Scheme 1 and Scheme 2, below, wherein the substituents are as described in Formula (1), above, and V is a leaving group, such as, for example, F, Cl, or $So_2CH_3$.

Scheme 1

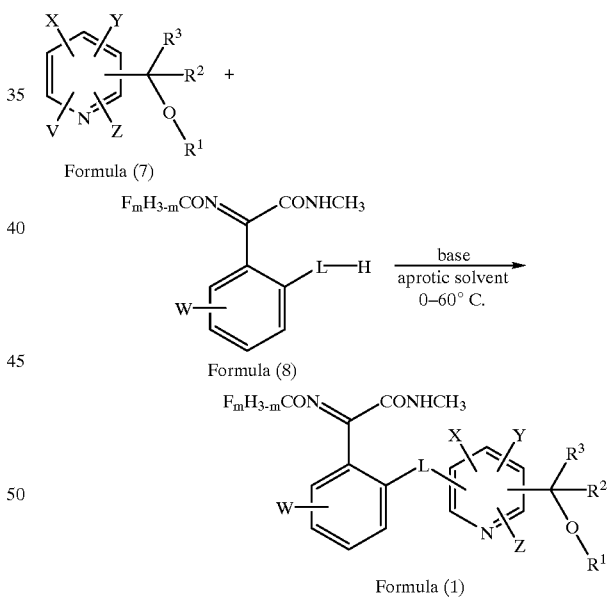

An compound of Formula (8) is reacted with an appropriately substituted pyridine derivative of Formula (7) in the presence of a base in an aprotic solvent. Examples of an appropriate solvent for this reaction would include, but are not restricted to, tetrahydrofuran, dimethyl sulphoxide, acetone, acetonitrile, dimethyl formamide, or N-methylpyrrolidinone. Examples of an appropriate base for this reaction would include, but are not restricted to, sodium hydride, potassium hydride, potassium carbonate, potassium t-butoxide, or a tertiary amine derivative such as triethylamine.

Scheme 2

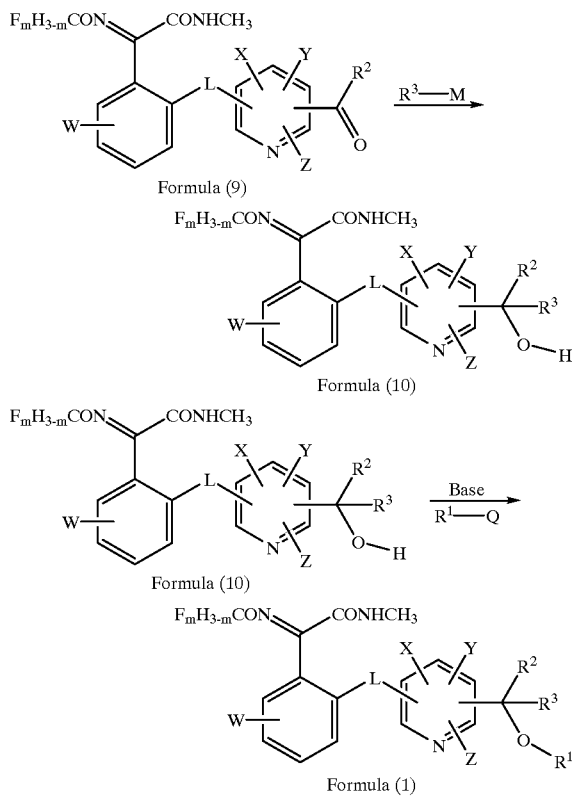

A ketone derivative of Formula (9) is reacted with an organometallic reagent of the form $R^3$-M in a compatible solvent to give an alcohol of the Formula (10). Examples of a group $R^3$-M would include, but are not restricted to, a Grignard reagent such as methyl magnesium bromide, an organolithium reagent such as phenyl lithium or a hydride transfer reagent such as sodium borohydride. Examples of a suitable solvent would be tetrahydrofuran, diethyl ether, or an appropriate alcohol, selected by compatibility with the reagent and the transformation being carried out. The compound of Formula (10) may be further derivatised by reaction with an appropriate alkylating or acylating reagent $R^1$-Q, optionally in the presence of an appropriate base. Compounds of the Formula $R^1$-Q would include, but are not restricted to acetic anhydride, benzyl bromide, dimethyl carbamoyl chloride, ethyl chloroformate, diethyl phosphoryl chloride, 5-chloro-3-methyl-2-methylsulphonylpyridine. Examples of a suitable base would include, but are not restricted to a tertiary amine such as triethylamine or pyridine, sodium carbonate, sodium hydride, potassium hydride, or potassium t-butoxide.

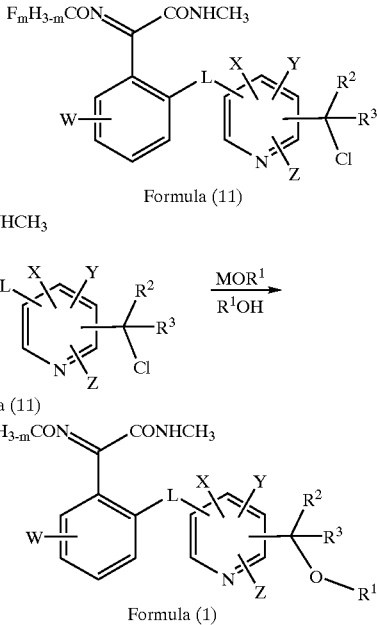

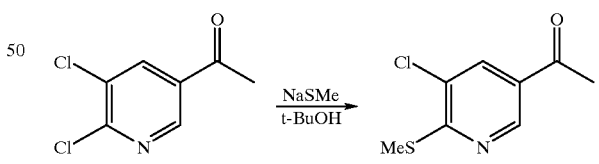

A compound of Formula (10) may also be reacted with a sulphonyl chloride of the formula $RSO_2Cl$ in the presence of a suitable base in a compatible solvent to give the corresponding chloride of Formula (11). Examples of a suitable sulphonyl chloride would be methanesulphonyl chloride, p-toluenesulphonyl chloride, and examples of a suitable base would be pyridine, triethylamine, or Hünig's base. The compound of formula (11) may be reacted further with a metal alkoxide salt in a compatible solvent to give a compound of Formula (1). Examples of a suitable metal alkoxide would include sodium methoxide, potassium ethoxide, or magnesium methoxide produced in situ by the addition of magnesium metal to methanol.

The following examples further illustrate this invention. The examples should not be construed as limiting the invention in any manner.

EXAMPLE 1

5-Acetyl-3-chloro-2-methylthiopyridine

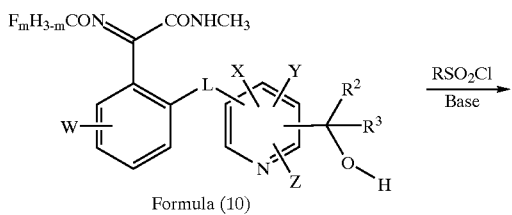

5-Acetyl-2,3-dichloropyridine (24.5 g, 0.129 mol) was slurried in t-butanol (200 mL) and sodium methanethiolate (10 g, 0.143 mol) was added. The mixture was heated under reflux conditions for two hours, cooled to room temperature, and diluted with water (200 mL) and ether (150 mL). This was separated and the aqueous phase extracted with ether (50 mL). The combined organic extracts were washed with water (100 mL) and saturated sodium chloride solution (100 mL), dried over anhydrous sodium sulphate, and evaporated to dryness to give the desired product (24.1 g, 94%) as a pale, low melting solid.

EXAMPLE 2

3-Chloro-5-(1-hydroxyethyl)-2-methylthiopyridine

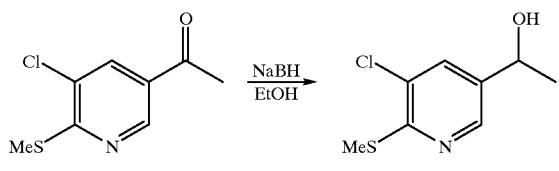

5-Acetyl-3-chloro-2-methylthiopyridine (24.1 g, 0.12 mol) was slurried in absolute ethanol (200 mL) and sodium borohydride (4.5 g, 0.118 mol) added in portions. The reaction mixture was stirred at room temperature for 48 hours and acidified to pH 2 with 2N hydrochloric acid. This was then diluted with water (200 mL) and the bulk of the ethanol evaporated under reduced pressure, the temperature of the mixture being maintained below 50° C. The reaction mixture was diluted with water (200 mL) and extracted twice with dichloromethane (15 mL). The combined organic extracts were washed with water (200 mL) and saturated sodium chloride solution (100 mL), dried over anhydrous sodium sulphate, and evaporated to dryness to give the desired product (21.9 g, 90%) as an orange oil.

EXAMPLE 3

5-(1-Benzyloxyethyl)-3-chloro-2-methylthiopyridine

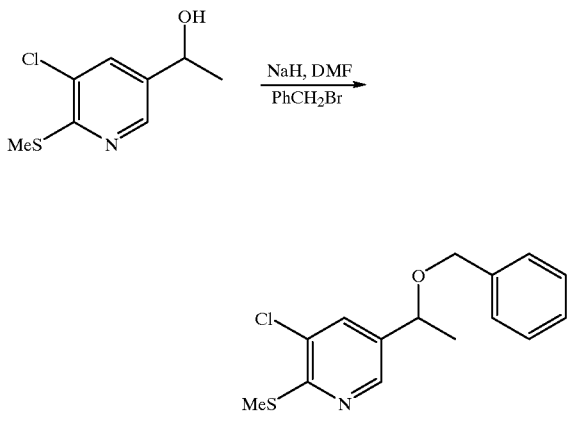

3-Chloro-5-(1-hydroxyethyl)-2-methylthiopyridine (21.9 g, 0.108 mol) was dissolved with stirring in anhydrous DMF (250 mL) and 60% sodium hydride (5 g, 0.125 mol) added in portions. The mixture was stirred at room temperature for 30 minutes and benzyl bromide (17.6 g, 0.103 mol) added dropwise. The mixture was then stirred at room temperature for four hours, diluted with water (400 mL) and extracted three times with ethyl acetate (100 mL). The combined organic extracts were washed twice with water (200 mL) and saturated sodium chloride solution (100 mL), dried over anhydrous sodium sulphate, and evaporated to dryness. Purification of the residue by chromatography over silica (0–5% ethyl acetate:hexane) gave the desired product (25.0 g, 79%) as a pale yellow oil.

EXAMPLE 4

5-(1-Benzyloxyethyl)-3-chloro-2-methylsulphonylpyridine

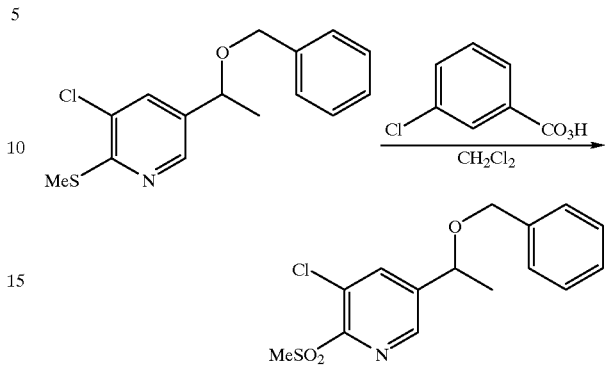

5-(1-Benzyloxyethyl)-3-chloro-2-methylthiopyridine (25 g, 0.085 mol) was dissolved with stirring in dichloromethane (600 mL) and 60% m-chloroperoxybenzoic acid (53.8 g, 0.19 mol) added in portions. The reaction mixture was stirred at room temperature overnight and 10% sodium carbonate solution (300 mL) added. The reaction mixture was stirred at room temperature for one hour, separated, and the organic phase washed four times with 2N sodium hydroxide solution (150 mL). It was then washed with saturated sodium chloride solution (150 mL), dried over anhydrous sodium sulphate, and evaporated under reduced pressure to give the product (26.5 g, 96%) as a clear viscous oil.

EXAMPLE 5

Benzeneacetamide, 2-[[[5-(1-benzyloxyethyl)-3-chloro-2-pyridinyl]oxy]methyl]-α-(methoxyimino)-N-methyl-

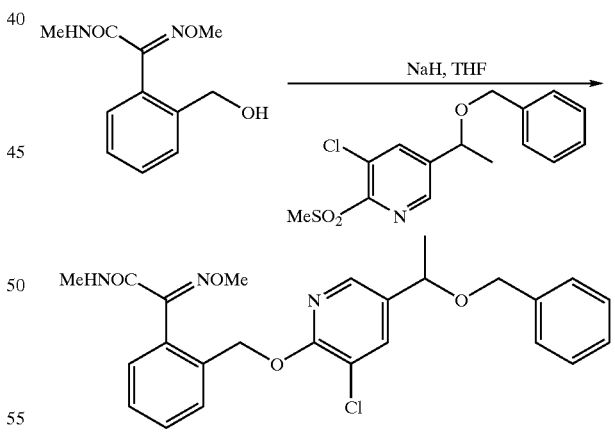

60% Sodium hydride (0.8 g, 0.2 mol) was washed twice with 50 mL portions of hexane and slurried in anhydrous THF (40 mL). 2-(Hydroxymethyl)-α-(methoxyimino)-N-methyl-benzeneacetamide (2.0 g, 0.009 mol) was then added in one portion and the mixture stirred at room temperature for 30 minutes. A solution of 5-(1-benzyloxyethyl)-3-chloro-2-methylsulphonylpyridine (3.0 g, 0.009 mol) in anhydrous THF (5 mL) was added and the mixture stirred at room temperature overnight. Water (100 mL) was added and the mixture extracted three times with ethyl acetate (50 mL).

The combined organic extracts were washed twice with water (100 mL) and then with saturated sodium chloride solution (50 mL). The solvent was evaporated under reduced pressure and the residue purified by chromatography over silica (30% ethyl acetate:hexane) to give the desired product (2.8 g, 66%) as a clear viscous gum.

EXAMPLE 6

Benzeneacetamide, 2-[[[3-chloro-5-hydroxyphenylmethyl-2-pyridinyl]oxy]methyl]-α-(methoxyimino)-N-methyl-

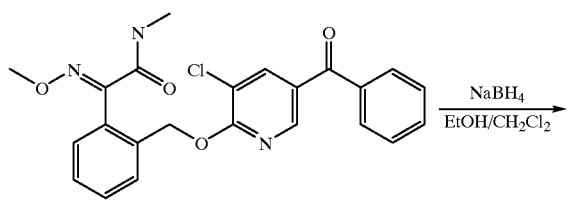

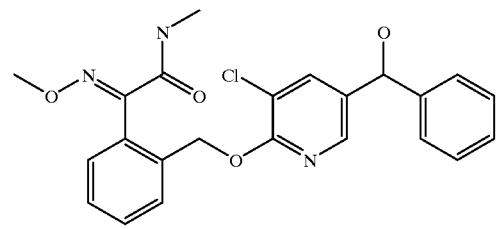

Sodium borohydride (129 mg; 3.4 mmol) was added in one portion to a solution of 2-[[[5-benzoyl-3-chloro-2-pyridinyl]oxy]methyl]-α-(methoxyimino)-N-methyl-benzeneacetamide (1.0 g; 2.3 mmol) in ethanol (23 mL) and dichloromethane (3 mL). The reaction was stirred for 10 minutes and quenched with 1N hydrochloric acid (2 mL). The reaction mixture was extracted twice with dichloromethane (20 mL), and the combined organic layers were washed with saturated sodium chloride solution, dried over anhydrous sodium sulphate, filtered and concentrated to give the desired product (993 mg; 99%) as a white foam.

EXAMPLE 7

Benzeneacetamide, 2-[[[5-[(acetyloxy)phenylmethyl]-3-chloro-2-pryridinyl]oxy]methyl]-α-(methoxyimino)-N-methyl-

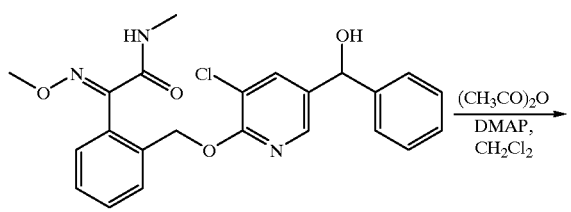

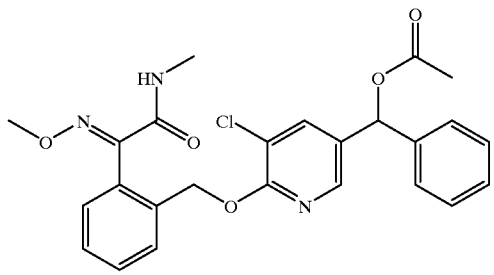

Acetic anhydride (0.17 mL; 1.8 mmol; 2 eq) was added dropwise at 0° C. to a solution of 2-[[[3-chloro-5-hydroxyphenylmethyl-2-pyridinyl]oxy]methyl]-α-(methoxyimino)-N-methyl-benzeneacetamide (400 mg; 0.91 mmol) and 4-dimethylaminopyridine (167 mg; 1.4 mmol; 1.5. eq) in dichloromethane (5 mL). The reaction mixture was warmed slowly to room temperature, and stirring continued for 10 minutes. The reaction mixture was quenched with water, partitioned, and the aqueous phase was extracted twice with dichloromethane. The combined organic layers were washed with 1N hydrochloric acid followed by saturated sodium chloride solution, then dried over anhydrous sodium sulphate, filtered and concentrated. Purification of the crude residue by flash chromatography using 50% EtOAc in hexanes provided the acetate as a sticky white foam (395 mg; 0.84 mmol; 93%).

EXAMPLE 8

Benzeneacetamide, 2-[[[3-chloro-5-[[(trifluoroacetyl)oxy]phenylmethyl]-2-pyridinyl]oxy]methyl]-α-(methoxyimino)-N-methyl-

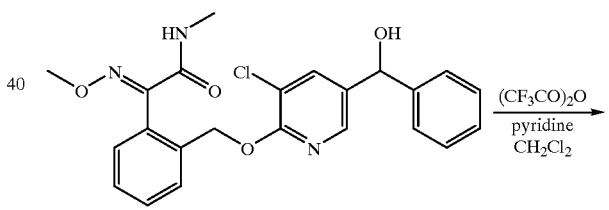

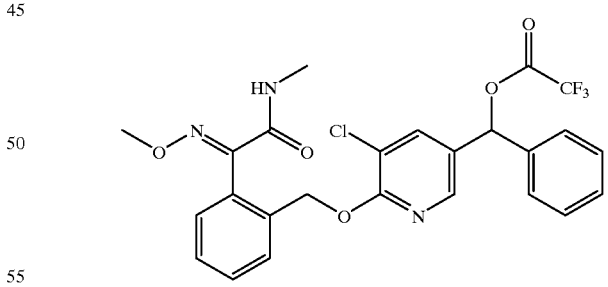

A solution of 2-[[[3-chloro-5-hydroxyphenylmethyl-2-pyridinyl]oxy]methyl]-α-(methoxyimino)-N-methyl-benzeneacetamide (515 mg; 1.2 mmol) and pyridine (0.38 mL; 4.7 mmol; 4 eq) in dichloromethane (5 mL) was cooled to 0° C. for the dropwise addition of trifluoroacetic anhydride (0.33 mL; 2.3 mmol.; 2 eq). The reaction was warmed slowly to room temperature and was quenched with water. Upon partitioning, the aqueous layer was extracted twice with dichloromethane (5 mL), and the combined aqueous layers were washed with saturated sodium chloride solution, dried over anhydrous sodium sulphate, filtered and concentrated. The crude product was placed under vacuum to remove the last traces of pyridine. The desired product (68 mg; 0.13 mmol; 11%) was isolated by chromatography over neutral alumina (50% ethyl acetate:hexane).

EXAMPLE 9

Benzeneacetamide, 2-[[[3-chloro-5-[[[(dimethylamino)carbonyl]oxy]phenylmethyl]-2-pyridinyl]oxy]methyl]-α-(methoxyimino)-N-methyl-

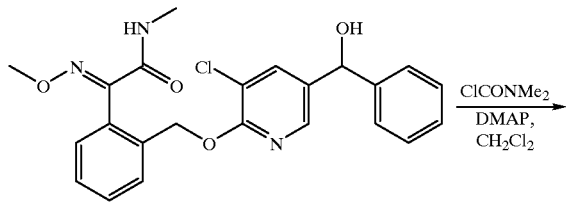

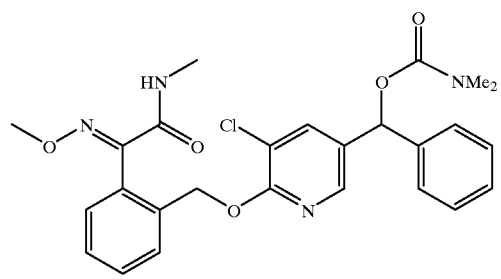

2-[[[3-chloro-5-hydroxyphenylmethyl-2-pyridinyl]oxy]methyl]-α-(methoxyimino)-N-methyl-benzeneacetamide (500 mg; 1.1 mmol) and 4-dimethylaminopyridine (836 mg; 6.8 mmol; 6 eq) were dissolved in dichloromethane (5 mL), and dimethylcarbamoyl chloride (0.31 mL; 3.4 mmol; 3 eq) was added at room temperature. The reaction mixture was heated to reflux for three hours, cooled back down to room temperature and quenched with water. The aqueous layer was extracted twice with dichloromethane (5 mL), and the combined organic layers were washed with 1N hydrochloric acid and saturated sodium chloride solution. They were then dried over anhydrous sodium sulphate, filtered and concentrated. The crude residue was purified by chromatography using 20% CH$_3$CN and dichloromethane to yield the desired product (192 mg 34%).

EXAMPLE 10

Benzeneacetamide, 2-[[[3-chloro-5-[(formyloxy)phenylmethyl]-2-pyridinyl]oxy]methyl]-α-(methoxyimino)-N-methyl-

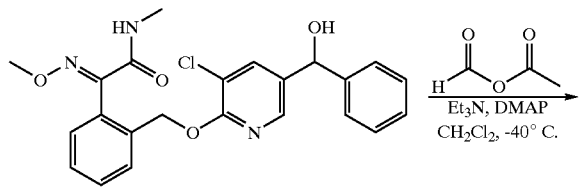

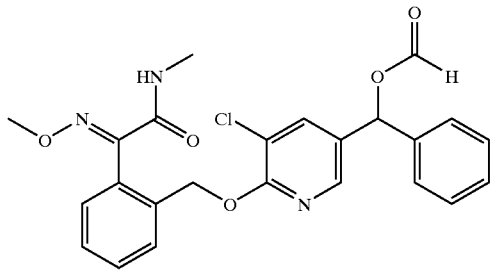

2-[[[3-chloro-5-hydroxyphenylmethyl-2-pyridinyl]oxy]methyl]-α-(methoxyimino)-N-methyl-benzeneacetamide (200 mg; 0.45 mmol), triethylamine (0.31 mL; 2.3 mmol; 5 eq) and 4-dimethylaminopyridine (44 mg; 0.36 mmol; 0.8 eq) were dissolved in dichloromethane (3.6 mL), and the resulting solution was cooled to −40° C. Acetyl formyl anhydride (0.19 mL; 1.2 mmol; 2.5 eq) was added dropwise to the reaction mixture, and stirring was continued at low temperature until the reaction was complete after 10 minutes. The cooling bath was removed, and saturated sodium bicarbonate was added to quench any excess reagent still present. The aqueous phase was extracted with dichloromethane (2×3 mL), and the combined organic layers were washed with 1N hydrochloric acid followed by saturated sodium chloride solution, dried over anhydrous sodium sulphate, filtered and concentrated. The crude product was purified by chromatography using 50% EtOAc in hexanes to give the product (541 mg, 100%) as a white foam.

EXAMPLE 11

Benzeneacetamide, 2-[[[3-chloro-5-[(diethylphosphonyl))phenylmethyl]-2-pyridinyl]oxy]methyl]-α-(methoxyimino)-N-methyl-

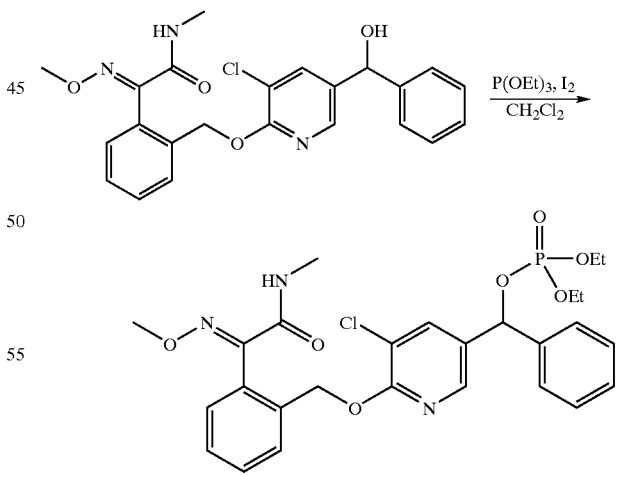

A solution of triethylphosphite (94 μL; 0.55 mmol; 1.2 eq) in dichloromethane (0.5 mL) was cooled to 0° C. for the addition of iodine (126 mg; 0.50 mmol; 1.1 eq). Stirring continued until the purple color dissipated, indicating complete formation of the phosphoryl iodide. This cold solution was transferred dropwise via cannula to a solution of 2-[[[3-chloro-5-hydroxyphenylmethyl-2-pyridinyl]oxy]methyl]-α-(methoxyimino)-N-methyl-benzeneacetamide (200 mg; 0.45 mmol) in pyridine (0.15 mL; 1.8 eq; 4 eq) and dichloromethane (4 mL). The alcohol solution turned yellow as the phosphoryl iodide reagent was added, but the color quickly dissipated as stirring continued. Upon completion of the addition, the reaction stirred at room temperature for another 30 minutes, turning brown in the process. It was quenched with saturated sodium bicarbonate solution and shaken with a crystal of sodium hydrogen sulphate. The aqueous phase was extracted with dichloromethane (2×3 mL), and the combined organic layers were washed with saturated sodium chloride solution, dried over anhydrous sodium sulphate, filtered and concentrated. The crude product was purified by chromatography using 70–80% EtOAc in hexanes to yield the desired product (130 mg, 50%) as a yellow-tinged foam.

EXAMPLE 12

Benzeneacetamide, 2-[[[3-chloro-5-[[(tetrahydro-2H-pyran-2-yl)oxy]phenylmethyl]-2-pyridinyl]oxy]methyl]-α-(methoxyimino)-N-methyl-

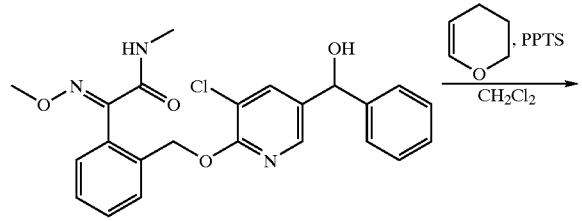

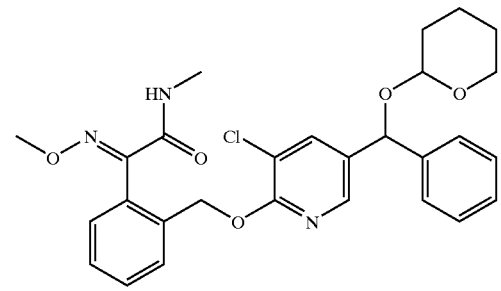

Dihydropyran (0.16 mL; 1.7 mmol; 1.5 eq) and a catalytic amount of pyridinium p-toluenesulphonate (28 mg; 0.11 mmol; 0.1 eq) were added to a solution of 2-[[[3-chloro-5-hydroxyphenylmethyl-2-pyridinyl]oxy]methyl]-α-(methoxyimino)-N-methyl-benzeneacetamide (500 mg; 1.1 mmol) in dichloromethane (8 mL). The reaction was stirred at room temperature overnight and was quenched with half-saturated sodium chloride solution (5 mL). The aqueous layer was extracted twice with diethyl ether (5 mL), and the combined organic layers were washed with saturated sodium chloride solution, dried over anhydrous sodium sulphate, filtered and concentrated. Purification of the crude product by chromatography using 50% EtOAc in hexanes gave the desired product (521 mg, 87%) as a white foam.

EXAMPLE 13

Benzeneacetamide, 2-[[[3-chloro-5-[[(triethylsilyl)oxy]phenylmethyl]-2-pyridinyl]oxy]methyl]-α-(methoxyimino)-N-methyl-

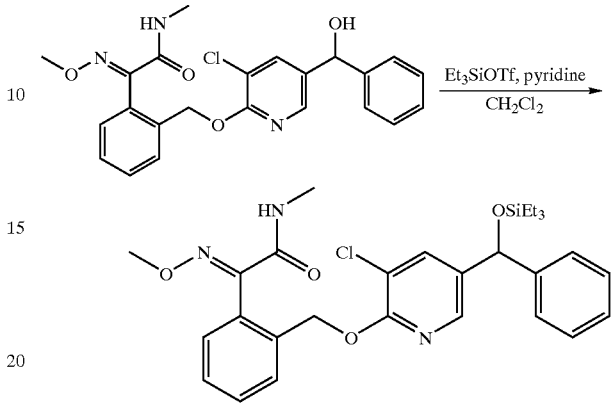

2-[[[3-chloro-5-hydroxyphenylmethyl-2-pyridinyl]oxy]methyl]-α-(methoxyimino)-N-methyl-benzeneacetamide (500 mg; 1.1 mmol) and pyridine (0.18 mL; 2.3 mmol; 2 eq) were dissolved in dichloromethane (5.7 mL) at room temperature. The resulting solution was cooled to −20° C. for the dropwise addition of triethylsilyl triflate (0.39 mL; 1.7 mmol; 1.5 eq). The bath was removed, and the reaction mixture was warmed slowly to room temperature where it stirred for 30 minutes. It was quenched with water (10 mL) and diluted with diethyl ether (10 mL). The aqueous phase was extracted with diethyl ether (5 mL), and the combined organic layers were washed with 1N hydrochloric acid followed by saturated sodium chloride solution, dried over anhydrous sodium sulphate, filtered and concentrated. The crude product was filtered through a plug of silica gel using diethyl ether to afford the desired product (511 mg, 81%) as a sticky, colorless oil.

EXAMPLE 14

Benzeneacetamide, 2-[[[3-chloro-5-(1-hydroxy-1-phenylethyl)-2-pyridinyl]oxy]methyl]-α-(methoxyimino)-N-methyl-

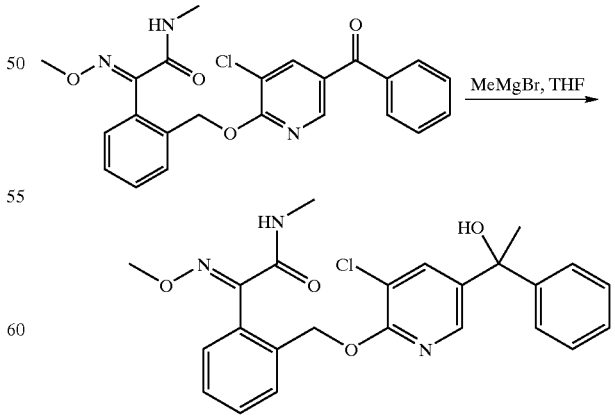

To a solution of 2-[[[5-benzoyl-3-chloro-2-pyridinyl]oxy]methyl]-α-(methoxyimino)-N-methyl-benzeneacetamide (1.0 g; 2.3 mmol) in THF (30 mL) was added a 3.0 M solution of methylmagnesium bromide in diethyl ether (4.6 mL; 13.7 mmol; 6 eq) at 0° C. The solution yellowed, and a precipitate appeared after a few minutes. The solution was warmed to room temperature where it was stirred for two hours. It was then cooled back down to 0° C. and quenched with aqueous ammonium chloride (20 mL). The aqueous layer was extracted twice with diethyl ether (10 mL), and the combined organic layers were washed with brine, dried over sodium sulfate and concentrated. The crude residue was passed through a plug of silica gel with the aid of diethyl ether to give the desired product (933 mg, 90%).

EXAMPLE 15

Benzeneacetamide, 2-[[[3-chloro-5-(1-phenylethenyl)-2-pyridinyl]oxy]methyl]-α-(methoxyimino)-N-methyl-

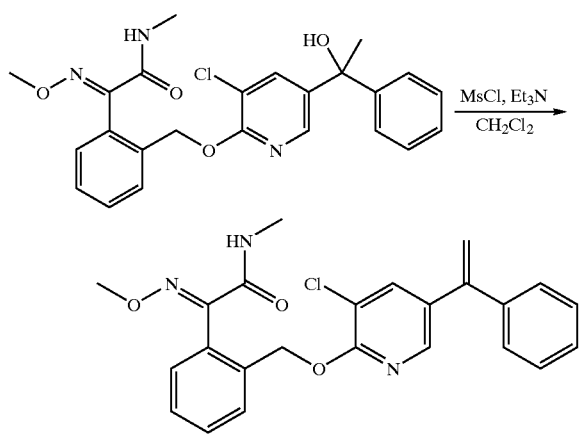

2-[[[3-chloro-5-(1-hydroxy-1-phenylethyl)-2-pyridinyl]oxy]methyl]-α-(methoxyimino)-N-methyl-benzeneacetamide (933 mg; 2.1 mmol) was dissolved in CH₂Cl₂ (10 mL), and triethylamine (0.87 mL; 6.2 mmol; 3 eq) was added at room temperature followed by methanesulfonyl chloride (0.40 mL; 5.2 mmol; 2.5 eq). The reaction mixture stirred for 30 minutes and was quenched with water. The aqueous layer was extracted twice with diethyl ether (20 mL), and the combined organic layers were washed with 1N HCl followed by brine and then dried over sodium sulfate and concentrated. The crude product was purified by flash column chromatography using 80% diethyl ether in hexanes to give the desired product (778 mg, 87%).

EXAMPLE 16

Benzeneacetamide, 2-[[[3-chloro-5-(1,2-dihydroxy-1-phenylethyl)-2-pyridinyl]oxy]methyl]-α-(methoxyimino)-N-methyl-

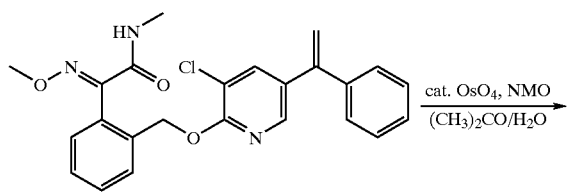

-continued

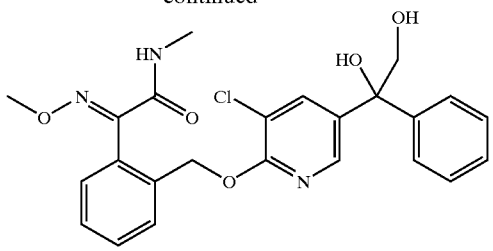

A 60% solution of N-methylmorpholine N-oxide in water (1.9 mL; 11.0 mmol; 1.5 eq) was added to a solution of 2-[[[3-chloro-5-(1-phenylethenyl)-2-pyridinyl]oxy]methyl]-α-(methoxyimino)-N-methyl-benzeneacetamide (3.2 g; 7.3 mmol) in aqueous acetone (30 mL acetone; 6 mL water) at room temperature. This was followed by the dropwise addition of a 4% solution of osmium tetroxide in water (1.43 mL; 0.18 mmol; 0.025 eq). The resulting reaction mixture stirred overnight, at which point sodium sulfite (250 mg) was added to quench any remaining oxidants. Stirring was continued until a black precipitate appeared, and the solution was diluted with water (15 mL) and extracted twice with EtOAc (30 mL). The combined organic layers were washed with saturated sodium chloride solution, dried over anhydrous sodium sulphate, filtered and concentrated. Purification by chromatography using a step gradient of 50–80% EtOAc in hexanes yielded the desired product as a brownish foam (3.5 g, 100%).

EXAMPLE 17

Benzeneacetamide, 2-[[[3-chloro-5-(2-hydroxy-1-[[(4-methylphenyl)sulfonyl]oxy]-2-phenylethyl)-2-pyridinyl]oxy]methyl]-α-(methoxyimino)-N-methyl-

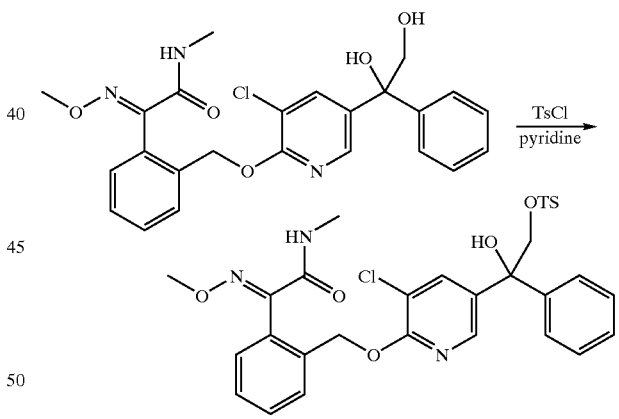

2-[[[3-chloro-5-(1,2-dihydroxy-1-phenylethyl)-2-pyridinyl]oxy]methyl]-α-(methoxyimino)-N-methyl-benzeneacetamide (1.22 g; 2.6 mmol) was dissolved in pyridine (6 mL) and the solution was cooled to 0° C. for the addition of p-toluenesulphonyl chloride (743 mg; 3.9 mmol; 1.5 eq). The bath was removed, and the reaction mixture stirred at room temperature overnight. It was then quenched with water (6 mL) and diluted with EtOAc (10 mL). The aqueous layer was extracted with EtOAc (6 mL), and the combined organic layers were washed with 1N hydrochloric acid followed by saturated sodium chloride solution, dried over anhydrous sodium sulphate, filtered and concentrated. The crude tosylate was purified by chromatography using 50% EtOAc in hexanes to afford 1.3 g (2.0 mmol; 80%) of the pure product as a white solid (M.P. 55–60° C.).

EXAMPLE 18

Benzeneacetamide, 2-[[[3-chloro-5-(2-phenyloxiranyl)-2-pyridinyl]oxy]methyl]-α-(methoxyimino)-N-methyl-

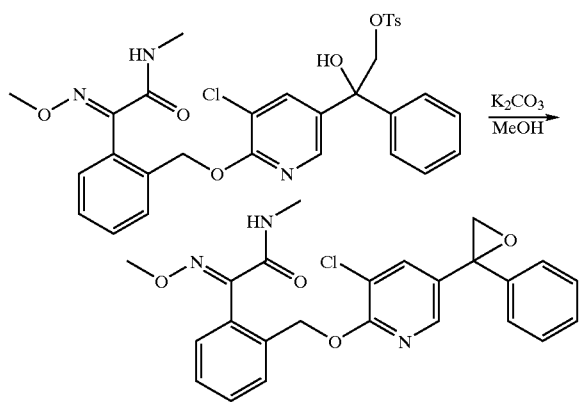

2-[[[3-chloro-5-(2-hydroxy-1-[[(4-methylphenyl)sulfonyl]oxy]-2-phenylethyl)-2-pyridinyl]oxy]methyl]-α-(methoxyimino)-N-methyl-benzeneacetamide (570 mg; 0.91 mmol) was dissolved in methanol (9 mL), and potassium carbonate (250 mg; 1.8 mmol; 2 eq) was added in one portion. Stirring continued at room temperature for about an hour, at which point the reaction mixture was diluted with water and the extracted with diethyl ether (10 mL). The combined organic layers were washed with saturated sodium chloride solution, dried over anhydrous sodium sulphate, filtered and concentrated to give the desired product (336 mg, 82%) as a white solid (M.P. 48–53° C.).

The following table identifies several compounds of Formula (1) of the formula below prepared analogous to the various procedures illustrated in the preceding examples:

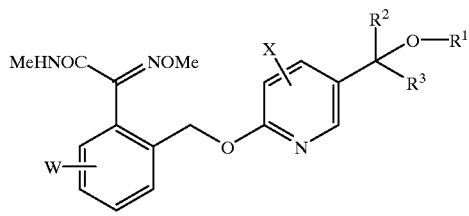

| Example | X | W | R¹ | R² | R³ |
|---|---|---|---|---|---|
| 1 | 3-chloro | H | H | H | phenyl |
| 2 | 3-chloro | H | t-butyldimethylsilyl | H | H |
| 3 | 3-chloro | H | Phenyl | H | H |
| 4 | 3-chloro | H | Benzoyl | H | H |
| 5 | 3-chloro | H | 2-pyridyl | H | H |
| 6 | 3-chloro | H | H | H | 2,4-dimethyl phenyl |
| 7 | 3-chloro | H | H | H | 4-fluoro phenyl |
| 8 | 3-chloro | H | Trimethylacetyl | H | H |
| 9 | 3-chloro | H | H | H | 4-chloro phenyl |
| 10 | 3-chloro | H | H | H | 4-t-butyl phenyl |
| 11 | 3-chloro | H | H | H | 4-methoxy phenyl |
| 12 | 3-chloro | H | H | H | 3-trifluoro methylphenyl |
| 13 | 3-methyl | H | H | H | phenyl |
| 14 | 3-methyl | H | H | H | 4-fluoro phenyl |
| 15 | 3-methyl | H | H | H | 4-chloro phenyl |
| 16 | 3-chloro | H | H | H | 4-trifluoro methoxyphenyl |
| 17 | 3-chloro | H | 4-methoxybenzyl | H | methyl |
| 18 | 3-methyl | fluoro | H | H | phenyl |
| 19 | 3-methyl | fluoro | H | H | 4-fluoro phenyl |
| 20 | 3-methyl | fluoro | H | H | 4-chloro phenyl |
| 21 | 3-methyl | chloro | H | H | phenyl |
| 22 | 3-methyl | chloro | H | H | 4-fluoro phenyl |

-continued

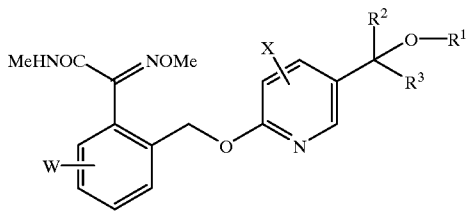

| Example | X | W | R¹ | R² | R³ |
|---|---|---|---|---|---|
| 23 | 3-methyl | chloro | H | H | 4-chloro phenyl |
| 24 | 3-chloro | H | Trimethylacetyl | H | methyl |
| 25 | 3-chloro | H | 4-methoxybenzyl | H | H |
| 26 | 3-chloro | H | H | methyl | phenyl |
| 27 | 3-chloro | H | 4-chlorobenzyl | H | methyl |
| 28 | 3-chloro | H | Acetyl | H | phenyl |
| 29 | 3-chloro | H | Benzoyl | H | phenyl |
| 30 | 3-chloro | H | Trimethylacetyl | H | phenyl |
| 31 | 3-chloro | fluoro | H | H | phenyl |
| 32 | 3-chloro | H | Isobutyryl | H | phenyl |
| 33 | 3-chloro | H | Ethoxycarbonyl | H | phenyl |
| 34 | 3-chloro | H | H | methyl | methyl |
| 35 | 3-chloro | H | Methyl | methyl | phenyl |
| 36 | 3-chloro | H | Propionyl | H | phenyl |
| 37 | 3-chloro | H | Trifluoroacetyl | H | phenyl |
| 38 | 3-chloro | H | Methyl | H | phenyl |
| 39 | 3-chloro | fluoro | Methyl | H | phenyl |
| 40 | 3-chloro | H | H | H | methyl |
| 41 | 3-chloro | H | n-pentyl | H | methyl |
| 42 | 3-chloro | H | H | ethyl | phenyl |
| 43 | 3-chloro | H | H | H | isopropyl |
| 44 | 3-chloro | H | 4-methylbenzyl | H | methyl |
| 45 | 3-chloro | H | Dimethylcarbamoyl | H | phenyl |
| 46 | 3-chloro | H | Acetyl | H | 4-fluoro phenyl |
| 47 | 3-chloro | H | Butyryl | H | phenyl |
| 48 | 3-chloro | H | Propionyl | H | 4-fluoro phenyl |
| 49 | 3-chloro | H | H | H | 2-naphthyl |
| 50 | 3-chloro | H | Butyryl | H | 4-fluoro phenyl |
| 51 | 3-chloro | H | H | H | 2-thienyl |
| 52 | 3-chloro | H | Benzyl | H | methyl |
| 53 | 3-chloro | H | Acetyl | methyl | phenyl |
| 54 | 3-chloro | H | Formyl | H | phenyl |
| 55 | 3-chloro | H | Diethylphosphoryl | H | phenyl |
| 56 | 3-chloro | H | Isopropoxycarbonyl | H | phenyl |
| 57 | 3-chloro | H | Tetrahydropyranyl | H | phenyl |
| 58 | 3-chloro | H | H | H | 3,4-methylene dioxyphenyl |
| 59 | 3-chloro | H | H | H | o-tolyl |
| 60 | 3-chloro | H | Acetyl | H | 3,4-methylene dioxyphenyl |
| 61 | 3-chloro | H | Acetyl | H | o-tolyl |
| 62 | 3-chloro | H | 3-methoxybenzyl | H | methyl |
| 63 | 3-chloro | H | Ethoxyacetyl | H | phenyl |
| 64 | 3-chloro | H | Methoxyacetyl | H | phenyl |
| 65 | 3-chloro | H | H | H | 2-fluoro phenyl |
| 66 | 3-chloro | H | H | H | 2-3-chloro phenyl |
| 67 | 3-chloro | H | Triethylsilyl | H | phenyl |
| 68 | 3-chloro | H | Methoxycarbonyl | H | phenyl |
| 69 | 3-chloro | H | Ethyl | H | phenyl |
| 70 | 3-chloro | H | H | H | p-tolyl |
| 71 | 3-chloro | H | Acetyl | H | p-tolyl |
| 72 | 3-chloro | H | H | H | phenyl |
| 73 | 3-chloro | H | H | H | 3-3-chloro phenyl |
| 74 | 3-chloro | H | Acetyl | H | 2-3-chloro phenyl |
| 75 | 3-chloro | H | Acetyl | H | 3-3-chloro phenyl |

-continued

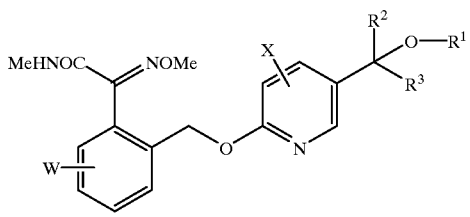

| Example | X | W | R¹ | R² | R³ |
|---|---|---|---|---|---|
| 76 | 3-chloro | H | Acetyl | H | phenyl |
| 77 | 3-chloro | H | Acetyl | H | 2-thienyl |
| 78 | 3-chloro | H | Acetyl | H | 4-trifluoro methoxyphenyl |
| 79 | 3-chloro | H | Methyl | H | 4-trifluoro methoxyphenyl |
| 80 | 3-chloro | H | n-butyl | H | methyl |
| 81 | 3-chloro | H | H | H | 2-trifluoro methylphenyl |
| 82 | 3-chloro | H | Acetyl | H | 2-fluoro phenyl |
| 83 | 3-chloro | H | Acetyl | H | 2-naphthyl |
| 84 | 3-chloro | H | H | H | m-tolyl |
| 85 | 3-chloro | H | H | H | m-tolyl |
| 86 | 3-chloro | H | H | hydroxy methyl | phenyl |
| 87 | 3-chloro | H | H | H | cyclohexyl |
| 88 | 3-chloro | H | Acetyl | H | 2-trifluoro methylphenyl |
| 89 | 3-chloro | H | 4-methoxyphenyl | H | methyl |
| 90 | 3-chloro | H | H | H | ethyl |
| 91 | 3-chloro | H | Acetyl | H | ethyl |
| 92 | 3-chloro | H | Acetyl | H | 2,4-dimethyl phenyl |
| 93 | 3-chloro | H | H | H | 3-fluoro phenyl |
| 94 | 3-chloro | H | H | 4-toluene sulphonyl oxymethyl | phenyl |
| 95 | 3-chloro | H | Acetyl | H | 4-methoxy phenyl |
| 96 | 3-chloro | H | Acetyl | H | 3-fluoro phenyl |
| 97 | 3-chloro | H | 2-methoxybenzyl | H | methyl |
| 98 | 3-methyl | H | Acetyl | H | phenyl |
| 99 | 3-chloro | H | Methyl | H | 2-fluoro phenyl |
| 100 | 3-chloro | H | H | H | 4-phenoxy phenyl |
| 101 | 3-chloro | H | 4-methoxybenzyl | H | phenyl |
| 102 | 3-chloro | H | H | H | 4-trifluoro methylphenyl |
| 103 | 3-chloro | H | H | H | 1-naphthyl |
| 104 | 3-chloro | H | 5-3-chloro-3-methyl-2-pyridyl | H | methyl |
| 105 | 3-chloro | H | H | H | 2-pyridyl |
| 106 | 3-chloro | H | Acetyl | H | m-tolyl |
| 107 | 3-chloro | H | Acetyl | acetoxy methyl | phenyl |
| 108 | 3-chloro | H | Acetyl | H | 2-pyridyl |
| 109 | 3-chloro | H | H | H | 3-thienyl |
| 110 | 3-chloro | H | H | H | 3,4-dimethoxy phenyl |
| 111 | 3-chloro | H | 2-fluoroethyl | H | methyl |
| 112 | 3-chloro | H | Acetyl | H | m-tolyl |
| 113 | 3-chloro | H | Ethyl | H | methyl |
| 114 | 3-chloro | H | Methyl | H | m-tolyl |
| 115 | 4-methoxy | H | Methyl | H | m-tolyl |
| 116 | 3-chloro | H | Acetyl | H | 3,4-dimethoxy phenyl |
| 117 | 3-chloro | H | Isopropyl | H | phenyl |
| 118 | 3-chloro | H | 2-ethoxyethyl | H | phenyl |
| 119 | 3-chloro | H | t-butyl | H | phenyl |
| 120 | 3-chloro | H | n-propyl | H | phenyl |
| 121 | 3-chloro | H | Acetyl | H | 3-thienyl |

-continued

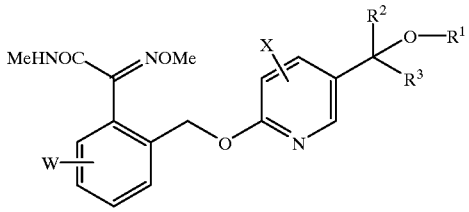

| Example | X | W | R¹ | R² | R³ |
|---|---|---|---|---|---|
| 122 | 3-chloro | H | Ethyl | methyl | phenyl |
| 123 | 3-chloro | H | | —C(CH₃)₂OCH₂— | phenyl |
| 124 | 3-chloro | H | | —CH₂— | phenyl |
| 125 | 3-chloro | H | | —C(=S)—OCH₂— | phenyl |

The compounds of Formula (1) thus produced are usually obtained as a mixture of the E and Z forms, which can then be separated, via standard means known in the art, into each of those forms, if desired.

The compounds of Formula (1) show strong fungicidal activity against a wide variety of fungi. The following tests illustrate the fungicidal efficacy of the compounds of this invention.

Fungicide Utility

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion. The compounds may also be employed effectively for the control of fungi on wood, leather, carpet backings, or in paint.

As used herein, the term "disease inhibiting and phytologically acceptable amount" refers to an amount of a compound of the present invention which kills or inhibits the plant disease for which control is desired but is not significantly toxic to the plant. This amount will generally be from about 1 to 1000 ppm, with 10 to 500 ppm being preferred. The exact concentration of compound required varies with the fungal disease to be controlled, the type of formulation employed, the method. of application, the particular plant species, climate conditions, and the like. A suitable application rate is typically in the range from about 0.10 to about 4 lb/A.

The compounds of the invention may also be used to protect stored grain and other non-plant loci from fungal infestation.

The following experiments were performed in the laboratory to determine the fungicidal efficacy of the compounds of the invention.

Compound Formulation

Compound formulation was accomplished by dissolving technical materials in acetone, with serial dilutions then made in acetone to obtain desired rates. Final treatment volumes were obtained by adding nine volumes 0.05% aqueous Tween-20 or Triton X-100, depending upon the pathogen.

Late Blight of Tomatoes (*Phytophthora infestans*—PHYTIN)

Tomatoes (cultivar Rutgers) were grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Phytophthora infestans*. The plants were then transferred to the greenhouse until disease developed on the untreated control plants.

Powdery Mildew of Wheat (*Erysiphe graminis*—ERYSGT)

Wheat (cultivar Monon) was grown in a soilless peat-based potting mixture (Metromix) until the seedlings were 1–2 leaf (BBCH 12). These plants were then sprayed to run off with the test compound at a rate of 100 ppm. After 24 hours the test plants were inoculated with *Erysiphe graminis* by dusting spores from stock plants onto the test plants. The plants were then transferred to the greenhouse until disease developed on the untreated control plants.

Glume Blotch of Wheat (*Leptosphaeria nodorum*—LEPTNO)

Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Leptosphaeria nodorum*. The plants were then transferred to the greenhouse until disease developed on the untreated control plants.

Brown Rust (*Puccinia recondita*—PUCCRT)

Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Puccinia recondita*. The plants were then transferred to the greenhouse until disease developed on the untreated control plants.

Septoria Leaf Spot (*Septoria tritici*—SEPTTR)

Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Septoria tritici*. The plants were then transferred to the greenhouse until disease developed on the untreated control plants.

The following table presents the activity of typical compounds of the present invention when evaluated in these experiments. The effectiveness of the test compounds in controlling disease was rated using the following scale:

blank space=not tested
−=0–24% control of plant disease
+=25–74% control of plant disease
++=75–100% control of plant disease

| Example | ERYSGT | PUCCRT | LEPTNO | SEPTTR | PHYTIN |
|---|---|---|---|---|---|
| 1 | ++ | ++ | ++ |  | ++ |
| 6 | ++ | ++ | − |  | ++ |
| 7 | ++ | ++ | ++ |  | ++ |
| 9 | ++ | ++ | ++ |  | ++ |
| 10 | ++ | ++ | ++ |  | ++ |
| 12 | ++ | ++ | ++ |  | ++ |
| 13 | ++ | ++ |  | ++ | ++ |
| 14 | ++ | ++ |  | ++ | ++ |
| 15 | ++ | ++ |  | ++ | ++ |
| 16 | ++ | ++ |  | ++ | − |
| 17 | ++ | ++ | ++ |  | − |
| 18 | ++ | ++ |  | ++ | ++ |
| 19 | ++ | ++ |  | ++ | + |
| 20 | ++ | ++ |  | ++ | ++ |
| 21 | ++ | ++ |  | ++ | ++ |
| 22 | ++ | ++ |  | ++ | ++ |
| 23 | ++ | ++ |  | ++ | ++ |
| 24 | ++ | ++ | ++ |  | − |
| 25 | ++ | ++ | ++ |  | + |
| 26 | ++ | ++ | ++ |  | ++ |
| 27 | ++ | ++ | ++ |  | − |
| 28 | − | ++ | ++ |  | − |
| 29 | + | ++ | ++ |  | + |
| 30 | + | ++ | ++ |  | ++ |
| 31 | + | ++ | − |  | ++ |
| 32 | − | ++ | − |  | − |
| 33 | + | ++ | ++ |  | ++ |
| 34 | − | ++ | + |  | + |
| 35 | ++ | ++ | ++ |  | − |
| 36 | + | ++ | ++ |  | ++ |
| 37 | + | ++ | ++ |  | ++ |
| 38 | + | ++ | ++ |  | − |
| 39 | + | ++ | ++ |  | − |
| 40 | + | ++ | ++ |  | + |
| 41 | ++ | ++ | ++ |  | − |
| 42 | ++ | ++ | ++ |  | ++ |
| 43 | ++ | ++ | + |  | ++ |
| 44 | ++ | ++ | ++ |  | ++ |
| 45 | ++ | ++ | ++ |  | ++ |
| 46 | ++ | − | ++ |  | − |
| 47 | ++ | ++ | ++ |  | ++ |
| 48 | ++ | ++ | ++ |  | ++ |
| 49 | ++ | ++ | ++ |  | ++ |
| 50 | ++ | ++ | ++ |  | ++ |
| 51 | ++ | ++ | ++ |  | ++ |
| 52 | ++ | ++ | ++ |  | − |
| 53 | ++ | ++ | ++ |  | ++ |
| 54 | ++ | ++ | ++ |  | ++ |
| 55 | ++ | ++ | ++ |  | ++ |
| 56 | ++ | ++ | ++ |  | ++ |
| 57 | ++ | ++ | ++ |  | ++ |
| 58 | ++ | ++ | ++ |  | ++ |
| 59 | ++ | ++ | ++ |  | ++ |
| 60 | ++ | ++ | ++ |  | ++ |
| 61 | ++ | ++ | ++ |  | ++ |
| 62 | ++ | ++ | ++ |  | − |
| 63 | ++ | ++ | ++ |  | ++ |
| 64 | ++ | ++ | + |  | ++ |
| 65 | ++ | ++ | ++ |  | ++ |
| 66 | ++ | ++ | ++ |  | ++ |
| 67 | ++ | ++ | ++ |  | ++ |
| 68 | ++ | ++ | − |  | ++ |
| 69 | ++ | ++ | ++ |  | − |
| 70 | ++ | ++ | ++ |  | ++ |
| 71 | ++ | ++ | ++ |  | ++ |
| 72 | ++ | ++ | ++ |  | ++ |
| 73 | ++ | ++ | ++ |  | ++ |
| 74 | ++ | ++ | ++ |  | ++ |
| 75 | ++ | ++ | ++ |  | ++ |
| 76 | ++ | ++ | ++ |  | ++ |
| 77 | ++ | ++ | ++ |  | ++ |
| 78 | ++ | ++ | ++ |  | ++ |
| 79 | ++ | ++ | ++ |  | − |
| 80 | ++ | ++ | ++ |  | − |
| 81 | ++ | ++ | + |  | ++ |
| 82 | ++ | ++ | ++ |  | ++ |
| 83 | ++ | ++ | ++ |  | ++ |
| 84 | ++ | ++ | − |  | ++ |
| 85 | ++ | ++ | ++ |  | − |
| 86 | − | ++ | − |  | ++ |
| 87 | ++ | ++ | ++ |  | ++ |
| 88 | ++ | ++ | ++ |  | ++ |
| 89 | ++ | ++ | ++ |  | ++ |
| 90 | ++ | ++ | + |  | ++ |
| 91 | ++ | ++ | ++ |  | ++ |
| 92 | ++ | ++ | ++ |  | ++ |
| 93 | ++ | ++ | ++ |  | ++ |
| 94 | ++ | ++ | ++ |  | ++ |
| 95 | ++ | ++ | ++ |  | ++ |
| 96 | ++ | ++ | ++ |  | ++ |
| 97 | ++ | ++ | ++ |  | − |
| 98 | ++ | ++ | ++ |  | ++ |
| 99 | ++ | ++ | ++ |  | − |
| 100 | ++ | ++ | ++ |  | ++ |
| 101 | ++ | ++ | + |  | ++ |
| 102 | ++ | ++ | ++ |  | ++ |
| 103 | + | ++ | ++ |  | ++ |
| 105 | ++ | ++ | ++ |  | ++ |
| 106 | ++ | ++ | ++ |  | ++ |
| 107 | ++ | ++ | ++ |  | ++ |
| 108 | ++ | ++ | ++ |  | ++ |
| 109 | ++ | ++ | ++ |  | ++ |
| 110 | ++ | ++ | ++ |  | ++ |
| 112 | ++ | ++ | ++ |  | ++ |
| 114 | ++ | ++ | ++ |  | − |
| 115 | + | ++ | ++ |  | − |
| 116 | ++ | ++ | ++ |  | + |
| 117 | ++ | ++ | ++ |  | − |
| 118 | ++ | ++ | ++ |  | − |
| 119 | ++ | ++ | ++ |  | ++ |
| 120 | ++ | − | + |  | + |
| 121 | ++ |  |  |  | ++ |
| 122 | ++ |  |  |  | − |
| 123 | ++ | ++ | ++ |  | ++ |
| 124 | ++ | ++ | ++ |  | ++ |
| 125 | ++ | ++ | ++ |  | ++ | blank space = not tested
− = 0–24% control of plant disease
+ = 25–74% control of plant disease
++ = 75–100% control of plant disease The compounds of this invention are preferably applied in the form of a composition comprising one or more of the compounds of Formula (1) with a phytologically-acceptable carrier. The compositions are either concentrated formulations which are dispersed in water or another liquid for application, or are dust or granular formulations which are applied without further treatment. The compositions are prepared according to procedures which are conventional in the agricultural chemical art, but which are novel and important because of the presence therein of the compounds of this invention. Some description of the formulation of the compositions is given to assure that agricultural chemists can readily prepare desired compositions.

The dispersions in which the compounds are applied are most often aqueous suspensions or emulsions prepared from concentrated formulations of the compounds. Such water-soluble, water suspendable, or emulsifiable formulations are either solids, usually known as wettable powders, or liquids, usually known as emulsifiable concentrates or aqueous suspensions. The present invention contemplates all vehicles by which the compounds of this invention can be formulated for delivery for use as a fungicide. As will be readily appreciated, any material to which these compounds can be added may be used, provided they yield the desired utility without significant interference with activity of the compounds of this invention as antifungal agents.

Wettable powders, which may be compacted to form water dispersible granules, comprise an intimate mixture of the active compound, an inert carrier and surfactants. The concentration of the active compound is usually from about 10% to about 90% w/w, more preferably about 25% to about 75% w/w. In the preparation of wettable powder compositions, the toxicant products can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the toxicant in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds of this invention comprise a convenient concentration, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilised with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of this invention, dispersed in an aqueous vehicle at a concentration in the range from about 5% to about 50% w/w. Suspensions are prepared by finely grinding the compound, and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions, which are particularly useful for applications to the soil. Granular compositions usually contain from about 0.5% to about 10% w/w of the compound, dispersed in an inert carrier which consists entirely or in large part of coarsely divided attapulgite, bentonite, diatomite, clay or a similar inexpensive substance. Such compositions are usually prepared by dissolving the compound in a suitable solvent and applying it to a granular carrier which has been preformed to the appropriate particle size, in the range of from about 0.5 to about 3 mm. Such compositions may also be formulated w by making a dough or paste of the carrier and compound, and crushing and drying to obtain the desired granular particle.

Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% w/w of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The composition may optionally include fungicidal combinations which comprise at least 1% of one or more of the compounds of this invention with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds in combination can generally be present in a ratio of from 1:100 to 100:1.

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds of this invention or compositions. The compounds are suitable for treatment of various plants at fungicidal levels, while exhibiting low phytotoxicity. The compounds are useful in a protectant or eradicant fashion. The compounds of this invention are applied by any of a variety of known techniques, either as the compounds or as compositions including the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds of this invention have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi which infect useful plant crops. Activity has been demonstrated for a variety of fungi. It will be understood by those in the art that the efficacy of the compounds of this invention for the foregoing fungi establishes the general utility of the compounds as fungicides.

The compounds of this invention have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the compounds of this invention, and compositions containing the same, may not be equally effective at similar concentrations or against the same fungal species. The compounds of this invention and compositions are effective in use with plants in a disease inhibiting and phytologically acceptable amount. The term "disease inhibiting and phytologically acceptable amount" refers to an amount of a compound which kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre.

What is claimed is:

1. A compound having the following formula

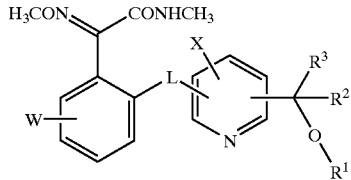

wherein
L is selected from the group consisting of —O—, —CH$_2$O—, and —OCH$_2$;
X is selected from the group consisting of H, C$_{1-6}$ alkyl, C$_{1-6}$ alkoxy, halo-C$_{1-6}$ alkyl, halo, and cyano;
W is selected from the group consisting of H, halo, C$_{1-4}$ alkyl, C$_{1-4}$ alkoxy, halo-C$_{1-4}$ alkyl, or C$_{1-4}$ alkylthio;
R$^1$ is selected from the group consisting of H, C$_{1-6}$ alkyl, halo C$_{1-6}$ alkyl, C$_{1-6}$ alkoxy C$_{1-3}$ alkyl, tri C$_{1-6}$ alkylsilyl, phenyl (which is optionally substituted with C$_{1-4}$ alkyl, halo, C$_{1-4}$ alkoxy, or halo C$_{1-4}$ alkyl), benzyl (which is optionally substituted with C$_{1-4}$ alkyl, halo, methoxy, or halo C$_{1-4}$ alkyl), di C$_{1-4}$ alkylphosphonyl, pyridyl (which is optionally substituted with C$_{1-4}$ alkyl or halo), tetrahydropyranyl, benzoyl (which is optionally substituted with C$_{1-6}$ alkyl, C$_{1-6}$ alkoxy, halo C$_{1-6}$ alkyl, halo C$_{1-6}$ alkoxy, halo, nitro, carbo C$_{1-6}$ alkoxy, or cyano), C$_{1-6}$ alkoxycarbonyl, or —CO—R$^4$;
R$^2$ is selected from the group consisting of H, C$_{1-3}$ alkyl, cyclo C$_{3-6}$ alkyl, hydroxy C$_{1-6}$ alkyl, or —CH$_2$OR$^5$; or
R$^1$ and R$^2$ together form a link of 1–3 atoms, where said link has at least one carbon atom and can have one oxygen atom, and where said link can be optionally substituted with oxygen and sulfur;
R$^3$ is an optionally substituted compound selected from the group consisting of thienyl or pyridyl, where said substituents are selected from the group consisting of C$_{1-6}$ alkyl, C$_{1-6}$ alkoxy, halo C$_{1-6}$ alkyl, halo C$_{1-6}$ alkoxy, halo, nitro, carbo C$_{1-6}$ alkoxy, or cyano;
R$^4$ is selected from the group consisting of H, C$_{1-6}$ alkyl, C$_{1-6}$ alkenyl, halo C$_{1-6}$ alkyl, C$_{1-6}$ alkoxy C$_{1-6}$ alkyl, phenyl (which is optionally substituted with C$_{1-4}$ alkyl, halo, methoxy, or halo C$_{1-6}$ alkyl), C$_{1-6}$ alkoxy, or di C$_{1-6}$ alkylamino; and
R$^5$ is selected from the group consisting of C$_{1-6}$ alkanoyl, benzoyl (which is optionally substituted with C$_{1-6}$ alkyl, C$_{1-6}$ alkoxy, halo C$_{1-6}$ alkyl, halo C$_{1-6}$ alkoxy, halo, nitro, carbo C$_{1-6}$ alkoxy, or cyano), C$_{1-6}$ alkylsulphonyl, benzenesulphonyl (which is optionally substituted with C$_{1-6}$ alkyl, C$_{1-6}$ alkoxy, halo C$_{1-6}$ alkyl, halo C$_{1-6}$ alkoxy, halo, nitro, carbo C$_{1-6}$ alkoxy, or cyano).

2. A compound according to claim 1 wherein
L is —CH$_2$O—;
X is selected from the group consisting of H, C$_{1-6}$ alkyl, C$_{1-6}$ alkoxy, halo-C$_{1-6}$ alkyl, and halo;
W is selected from the group consisting of H and halo;
R$^1$ is selected from the group consisting of H, C$_{1-6}$ alkyl, halo C$_{1-6}$ alkyl, C$_{1-6}$ alkoxy C$_{1-3}$ alkyl, tri C$_{1-6}$ alkylsilyl, phenyl (which is optionally substituted with C$_{1-4}$ alkoxy), benzyl (which is optionally substituted with C$_{1-4}$ alkyl, halo, or methoxy), di C$_{1-4}$ alkylphosphonyl, pyridyl (which is optionally substituted with C$_{1-4}$ alkyl or halo), tetrahydropyranyl, benzoyl, C$_{1-6}$ alkoxycarbonyl, or —CO—R$^4$;
R$^2$ is selected from the group consisting of H, C$_{1-3}$ alkyl, hydroxy C$_{1-6}$ alkyl, or —CH$_2$OR$^5$; or
R$^1$ and R$^2$ together form a link of 1–3 atoms, where said link has at least one carbon atom and can have one oxygen atom, and where said link can be optionally substituted with oxygen and sulfur;
R$^3$ is selected from the group consisting of thienyl or pyridyl;
R$^4$ is selected from the group consisting of H, C$_{1-6}$ alkyl, C$_{1-6}$ alkenyl, halo C$_{1-6}$ alkyl, C$_{1-6}$ alkoxy C$_{1-6}$ alkyl, phenyl, C$_{1-6}$ alkoxy), or di C$_{1-6}$ alkylamino; and
R$^5$ is selected from the group consisting of C$_{1-6}$ alkanoyl, benzenesulphonyl (which is optionally substituted with C$_{1-6}$ alkyl).

3. A method comprising applying to a locus a fungicidally-effective amount of the compound according to claim 1.

4. A method comprising applying to a locus a fungicidally-effective amount of the compound according to claim 2.

* * * * *